United States Patent
Zoabi et al.

(10) Patent No.: US 10,420,612 B2
(45) Date of Patent: Sep. 24, 2019

(54) INTERACTIVE ANATOMICAL MAPPING AND ESTIMATION OF ANATOMICAL MAPPING QUALITY

(71) Applicant: BIOSENSE WEBSTER (ISRAEL) LTD., Yokneam (IL)

(72) Inventors: Akram Zoabi, Kfar Masser (IL); Fady Massarwi, Baka Al Gharbiyya (IL)

(73) Assignee: Biosense Webster (Isreal) Ltd., Yokneam (IL)

( * ) Notice: Subject to any disclaimer, the term of this patent is extended or adjusted under 35 U.S.C. 154(b) by 208 days.

(21) Appl. No.: 15/387,986

(22) Filed: Dec. 22, 2016

(65) Prior Publication Data

US 2018/0177552 A1    Jun. 28, 2018

(51) Int. Cl.
| | | |
|---|---|---|
| *A61B 34/10* | (2016.01) | |
| *A61B 5/00* | (2006.01) | |
| *A61B 5/042* | (2006.01) | |
| *A61B 34/00* | (2016.01) | |
| *A61B 90/00* | (2016.01) | |
| *A61B 34/20* | (2016.01) | |
| *A61B 5/04* | (2006.01) | |
| *A61B 5/044* | (2006.01) | |

(52) U.S. Cl.
CPC .............. *A61B 34/10* (2016.02); *A61B 5/042* (2013.01); *A61B 5/044* (2013.01); *A61B 5/04012* (2013.01); *A61B 5/6852* (2013.01); *A61B 5/743* (2013.01); *A61B 34/20* (2016.02); *A61B 34/25* (2016.02); *A61B 90/37* (2016.02); *A61B 2034/105* (2016.02); *A61B 2034/252* (2016.02); *A61B 2090/367* (2016.02)

(58) Field of Classification Search
USPC ......................................................... 607/119
See application file for complete search history.

(56) References Cited

U.S. PATENT DOCUMENTS

| | | |
|---|---|---|
| 5,391,199 A | 2/1995 | Ben-Haim |
| 5,637,900 A | 6/1997 | McGee et al. |
| 6,239,724 B1 | 5/2001 | Doron et al. |
| 6,332,089 B1 | 12/2001 | Acker et al. |
| 6,484,118 B1 | 11/2002 | Govari |
| 6,618,612 B1 | 9/2003 | Acker et al. |
| 6,690,963 B2 | 2/2004 | Ben-Haim et al. |
| 7,604,601 B2 | 10/2009 | Altmann et al. |

(Continued)

FOREIGN PATENT DOCUMENTS

| | | |
|---|---|---|
| EP | 2 837 328 A1 | 2/2015 |
| WO | WO 96/05768 A1 | 2/1996 |

OTHER PUBLICATIONS

European Search Report dated May 25, 2018 from corresponding European Patent Application No. 17209566.3.

*Primary Examiner* — Nicole F Lavert
(74) *Attorney, Agent, or Firm* — Lewis Roca Rothgerber Christie LLP

(57) ABSTRACT

A method includes receiving an anatomical mapping that includes multiple measurements acquired at multiple respective locations within an organ of a patient. An estimated surface of the organ is computed based on the measurements. A three-dimensional (3D) shell of the organ, which extends inwards from the estimated surface of the organ and has a predefined thickness, is defined. A quality of the anatomical mapping is estimated based on the measurements whose locations fall within the 3D shell.

12 Claims, 4 Drawing Sheets

(56) References Cited

U.S. PATENT DOCUMENTS

| | | |
|---|---|---|
| 8,106,905 B2 | 1/2012 | Markowitz et al. |
| 8,412,307 B2 | 4/2013 | Willis et al. |
| 8,457,371 B2 | 6/2013 | Markowitz et al. |
| 8,494,608 B2 | 7/2013 | Markowitz et al. |
| 8,708,902 B2 | 4/2014 | Heimbecher |
| 8,744,566 B2 | 6/2014 | Harlev et al. |
| 8,887,736 B2 | 11/2014 | Markowitz et al. |
| 8,900,225 B2 | 12/2014 | Bar-Tal et al. |
| 9,204,935 B2 | 12/2015 | Hauck et al. |
| 2002/0065455 A1 | 5/2002 | Ben-Haim et al. |
| 2003/0120150 A1 | 6/2003 | Govari |
| 2004/0068178 A1 | 4/2004 | Govari |
| 2006/0116576 A1 | 6/2006 | McGee et al. |
| 2009/0099468 A1 | 4/2009 | Thiagalingam et al. |
| 2011/0152684 A1 | 6/2011 | Altmann et al. |
| 2012/0316431 A1 | 12/2012 | Shachar et al. |
| 2014/0235998 A1* | 8/2014 | Kim .................. A61B 6/5247 600/424 |
| 2015/0018698 A1 | 1/2015 | Safran et al. |
| 2015/0119738 A1 | 4/2015 | Deno |
| 2016/0073960 A1 | 3/2016 | Jung et al. |

\* cited by examiner

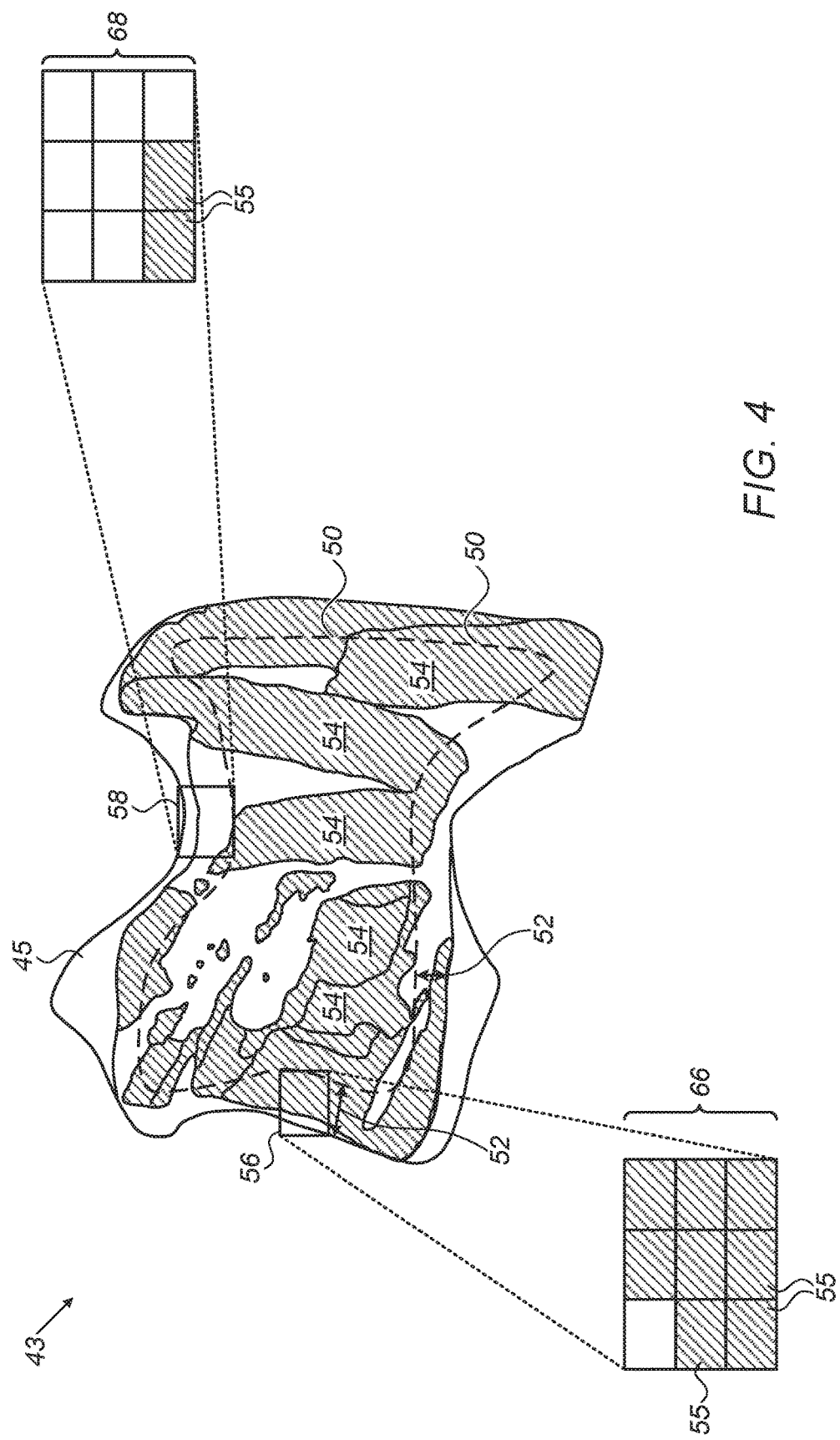

INTERACTIVE ANATOMICAL MAPPING AND ESTIMATION OF ANATOMICAL MAPPING QUALITY

FIELD OF THE INVENTION

The present invention relates generally to anatomical mapping, and particularly to methods and systems for interactive anatomical mapping and estimation of anatomical mapping quality.

BACKGROUND OF THE INVENTION

Anatomical mapping may be used for diagnosing various types of medical conditions, such as cardiac arrhythmia. Various techniques may be applied for deriving an anatomical mapping and for controlling the mapping procedure.

For example, U.S. Pat. No. 8,744,566, whose disclosure is incorporated herein by reference, describes methods and systems for the determination and representation of anatomical information. The methods and systems include generating anatomical information of the heart, based on positions of the catheter electrodes and the electrical signals from the electrodes at the determined subset of electrode positions.

U.S. Pat. No. 8,457,371, whose disclosure is incorporated herein by reference, describes method and apparatus for mapping a structure. The mapping apparatus may include one or more electrodes that can sense a voltage that can be correlated to a three dimensional location of the electrode at the time of the sensing or measurement. A map of an area or volume can be determined based upon the sensing of the plurality of points without the use of an imaging device. An implantable medical device can then be navigated relative to the mapping data.

U.S. Pat. No. 8,900,225, whose disclosure is incorporated herein by reference, describes a method for performing a medical procedure that includes bringing a probe into contact with an organ in a body of a patient. A map of the organ is displayed, and the location of the probe relative to the map is tracked.

U.S. Patent Application Publication 2009/0099468, now abandoned, whose disclosure is incorporated herein by reference, describes a method, an apparatus, and a computer program product for automated processing of intra-cardiac electrophysiological data. The method includes recording electro-gram data, defining at least one reference channel containing a reference beat for determining temporal locations, creating an index of the temporal locations, analyzing in real-time at least one electrophysiological feature, and providing an updated index and results of the analysis.

SUMMARY OF THE INVENTION

An embodiment of the present invention that is described herein provides a method including receiving an anatomical mapping that includes multiple measurements acquired at multiple respective locations within an organ of a patient. An estimated surface of the organ is computed based on the measurements. A three-dimensional (3D) shell of the organ, which extends inwards from the estimated surface of the organ and has a predefined thickness, is defined. A quality of the anatomical mapping is estimated based on the measurements whose locations fall within the 3D shell.

In some embodiments, defining the 3D shell includes forming, at a predefined distance inwards from the estimated surface, a virtual surface confining the shell between the estimated surface and the virtual surface. In other embodiments, estimating the quality of the anatomical mapping includes counting a number of the measurements whose locations fall within at least part of the shell. In yet other embodiments, the shell includes multiple volume pixels (voxels), and estimating the quality is based on a number of the voxels, within the at least part of the shell, in which the measurements fall.

In an embodiment, the shell includes a surface including multiple pixels, and estimating the quality is based on a number of the pixels, within the at least part of the shell, in which the measurements fall. In another embodiment, the organ includes a cavity of a heart.

There is additionally provided, in accordance with another embodiment of the present invention, a method including receiving a partial anatomical mapping that includes multiple measurements acquired at multiple respective locations within an organ of a patient. An estimated partial surface of the organ is computed based on the measurements. Based on the measurements, an unvisited region of the organ, which was not yet mapped by the partial anatomical mapping, is identified. The unvisited region is indicated to a user, so as to assist the user in mapping the unvisited region and extending the estimated partial surface.

In some embodiments, the multiple measurements are acquired using a distal end of a catheter, and indicating the unvisited region includes displaying a graphical indication indicative of a direction to which the user is to move the distal end in order to map the unvisited region. In other embodiments, the method includes overlaying a grid of volume pixels (voxels) within at least part of the organ, and identifying the unvisited region includes identifying one or more voxels of the grid that were not yet mapped by the partial anatomical mapping. In yet other embodiments, the method includes defining a given volume that extends outwards from a catheter distal end that is used for acquiring the measurements, and identifying the unvisited region includes identifying, within the given volume, locations that were not yet visited by the distal end.

There is additionally provided, in accordance with an embodiment of the present invention, an apparatus including an interface and a processor. The processor is configured to receive from the interface an anatomical mapping, including multiple measurements acquired at multiple respective locations within an organ of a patient, to compute an estimated surface of the organ based on the measurements, to define a three-dimensional (3D) shell of the organ, which extends inwards from the estimated surface of the organ and has a predefined thickness, and to estimate a quality of the anatomical mapping, based on the measurements whose locations fall within the 3D shell.

There is further provided, in accordance with an embodiment of the present invention, an apparatus including an interface and a processor. The processor is configured to receive a partial anatomical mapping, including multiple measurements acquired at multiple respective locations within an organ of a patient, to compute an estimated partial surface of the organ based on the measurements, to identify, based on the measurements, an unvisited region of the organ that was not yet mapped by the partial anatomical mapping, and to indicate on the output device the unvisited region to a user, so as to assist the user in mapping the unvisited region and extending the estimated partial surface.

The present invention will be more fully understood from the following detailed description of the embodiments thereof, taken together with the drawings in which:

BRIEF DESCRIPTION OF THE DRAWINGS

FIG. 4 is a schematic, pictorial illustration of a scheme for estimating the quality of an anatomical map, in accordance with an embodiment of the present invention.

DETAILED DESCRIPTION OF EMBODIMENTS

Overview

In some medical procedures, such as cardiac ablation, a medical probe is navigated into a patient heart based on an estimated anatomical map of the heart. Estimating the anatomical map may be carried out by inserting a catheter having sensing electrodes disposed on its distal end, and measuring certain signals at multiple locations of tissue on the heart inner surface using the electrodes. Mapping algorithms that are based on such measurements, such as fast anatomical mapping (FAM), are known in the art. The FAM method may provide a physician with additional mapping capabilities, such as electro-physiological (EP) mapping that may be used for the cardiac ablation.

During the FAM procedure, a physician navigates the distal end of the catheter to desired locations distributed across the tissue in question so as to collect anatomical signals therefrom. In principle, the FAM may provide the physician with a surface representing an estimated anatomical mapping of the tissue in question. This surface will be used by the physician during the EP mapping and ablation procedures, therefore it is important to monitor the quality of the anatomical mapping before starting the EP procedure.

Embodiments of the present invention that are described hereinbelow provide improved techniques for interactive anatomical mapping. The disclosed techniques may be used for indicating to the physician unmapped ("unvisited") regions of the heart surface. In an embodiment, after receiving partial measurements of the anatomical mapping, the processor computes a partial surface of the tissue and identifies, based on the partial surface, one or more unvisited regions in the tissue for further anatomical mapping.

In an embodiment, the processor is configured to display a graphical indication that directs the physician to the unvisited regions, so as to assist the physician in mapping the entire surface. After concluding the anatomical mapping, the processor displays the estimated anatomical mapping of the entire surface.

In another embodiment, the processor is configured to estimate the quality of the anatomical mapping by defining a three-dimensional (3D) shell which extends inwards from the estimated anatomical surface. For example, the processor may define a virtual surface parallel to the estimated surface so that the 3D shell is the volume confined between the two surfaces. In some embodiments, the processor estimates the quality of the anatomical mapping based on the number of mapping measurements whose locations fall within the predefined volume.

The disclosed techniques provide real-time visualization of the ongoing mapping procedure, and provides feedback regarding the quality of the estimated anatomical surface, thereby obtaining high quality mapping and shortening the procedure cycle time.

System Description

Figure 1:
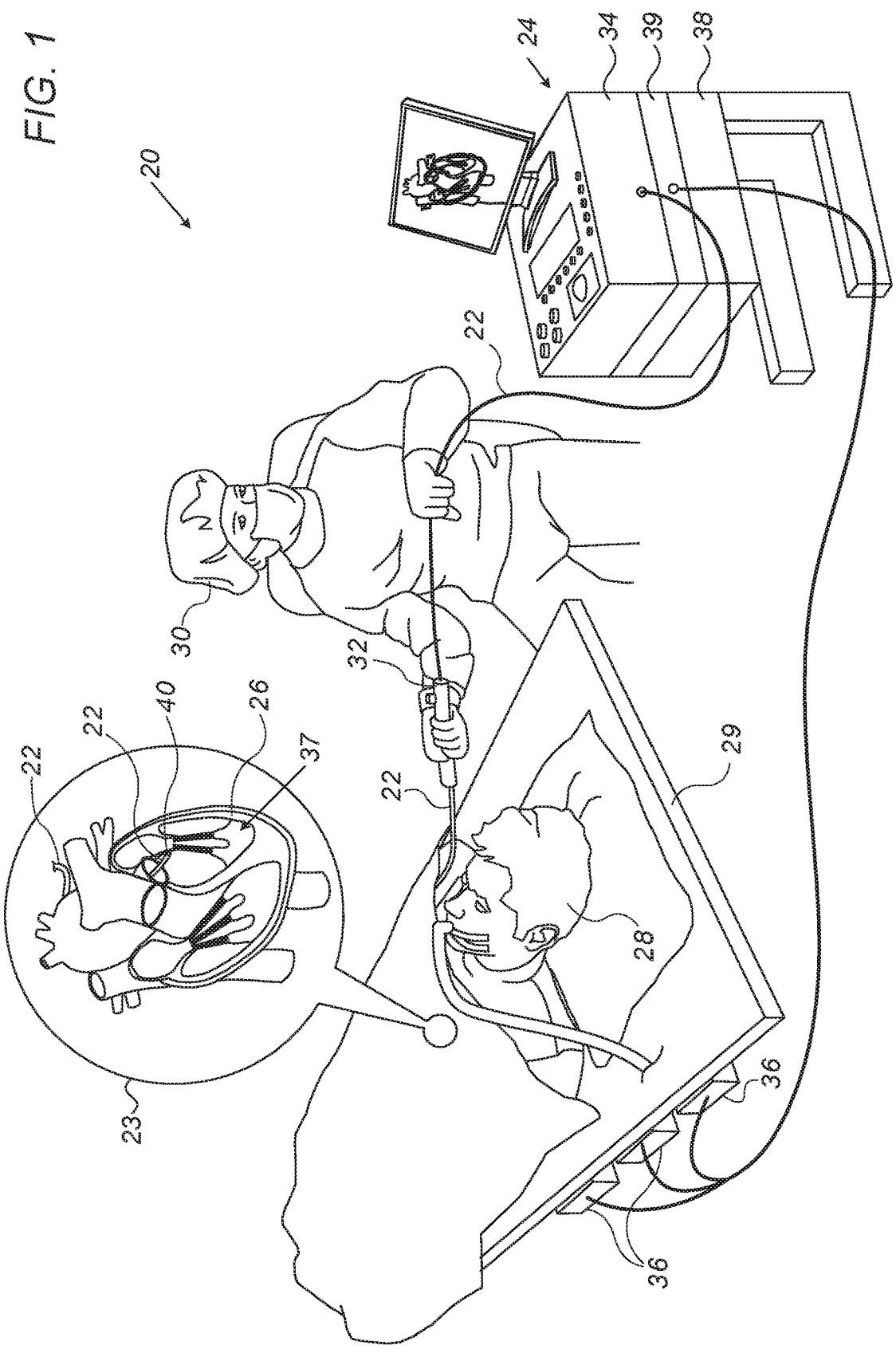
FIG. 1 is a schematic, pictorial illustration of a catheter-based tracking and ablation system that employs anatomical mapping, in accordance with an embodiment of the present invention.

FIG. 1 is a schematic, pictorial illustration of a catheter-based tracking and ablation system 20, in accordance with an embodiment of the present invention. System 20 comprises a catheter 22, in the present example a cardiac catheter, and a control console 24. In the embodiment described herein, catheter 22 may be used for any suitable therapeutic and/or diagnostic purposes, such as anatomical mapping of a cavity 37 in a heart 26.

Figure 2:
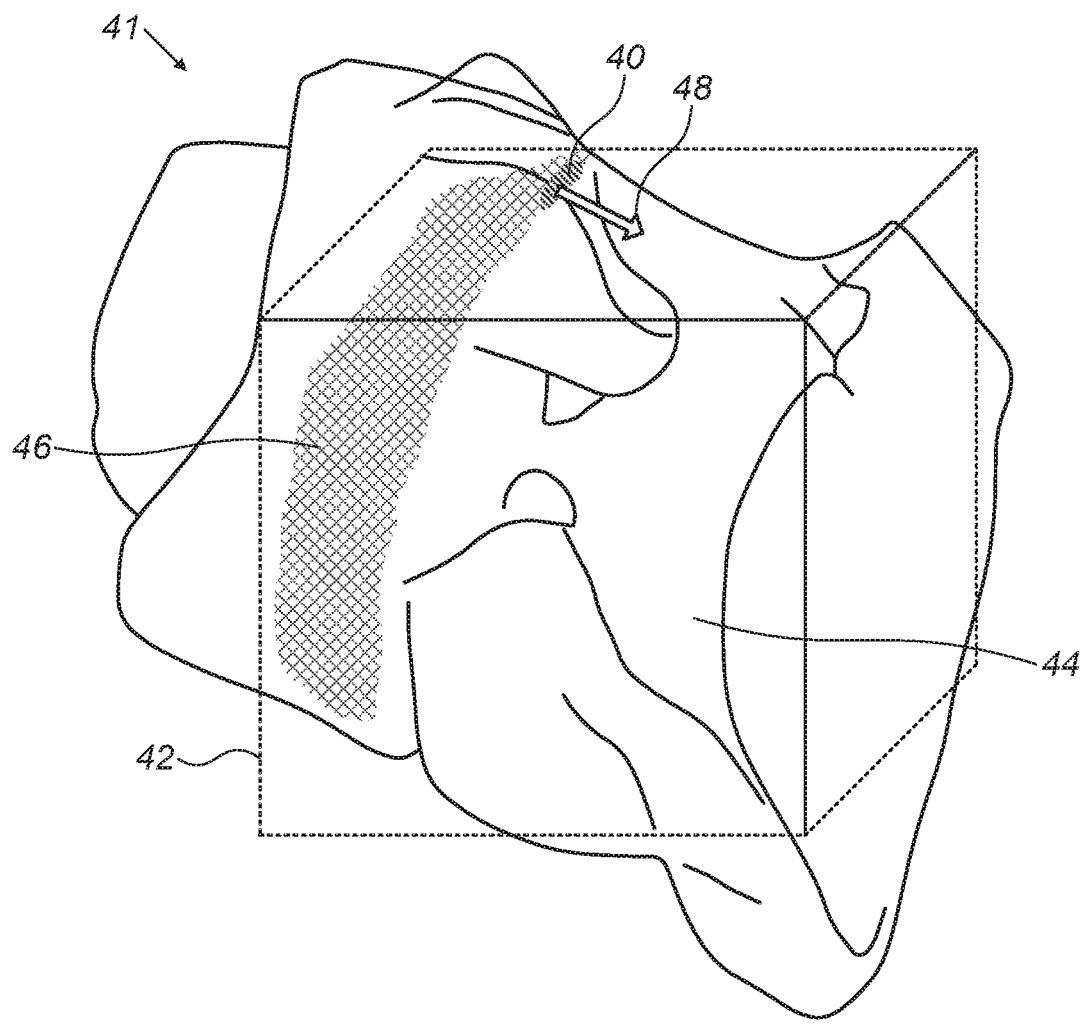
FIG. 2 is a schematic, pictorial illustration of an anatomical map of an inner surface of a heart, and a visualization scheme that directs a user toward unmapped areas of the surface, in accordance with an embodiment of the present invention.
Figure 3:
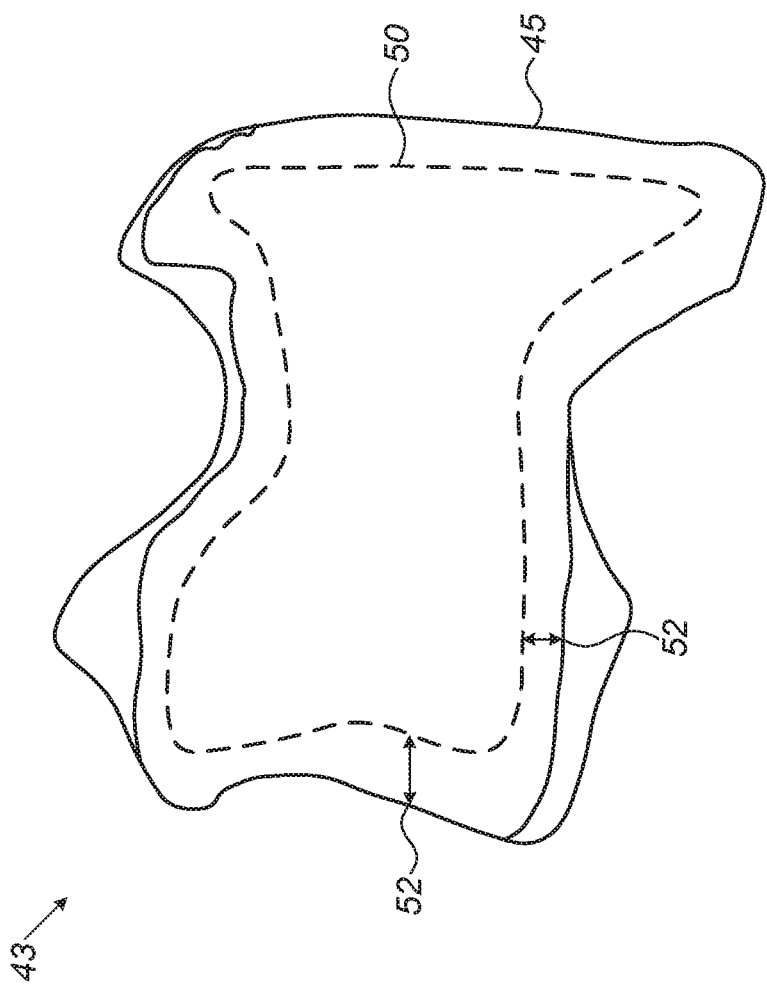
FIG. 3 is a schematic, pictorial illustration of an estimated anatomical map of an inner surface of a heart, in accordance with an embodiment of the present invention.

Console 24 comprises a processor 39, typically a general-purpose computer, with suitable front end and interface circuits 38 for receiving signals via catheter 22 and for controlling the other components of system 20 described herein. Console 24 further comprises a user display 35, also referred to as an output device, which is configured to display tools for assisting in anatomical mapping as shown in FIGS. 2-4 below.

The procedure of anatomical mapping is carried out using distal end 40 that collects multiple measurements at respective locations of the heart tissue, the measurements outcomes are referred to herein as map points. Each map point comprises a three-dimensional (3D) coordinate on the tissue of cavity 37 and a respective measurement of some physiological property that is measured at this coordinate.

In some embodiments, processor 39 is configured to construct, based on the measurements or map points, an estimated anatomical surface (shown in FIGS. 3 and 4), and present the estimated anatomical surface to physician 30 on display 35. In constructing the estimated anatomical surface, processor 39 may apply to the measurements a procedure such as the Fast Anatomical Mapping (FAM) procedure, which is described, for example, in U.S. Patent Application Publication 2011/0152684, whose disclosure is incorporated herein by reference.

In some medical procedures, such as ablation of tissue, physician 30 creates an anatomical map of the tissue to be ablated in advance. To perform the anatomical mapping, physician 30 inserts catheter 22 through the vascular system of a patient 28 lying on a table 29. Catheter 22 comprises one or more electrodes (not shown) typically fitted at a distal end 40. The electrodes are configured to sense the tissue of cavity 37 of heart 26. Physician 30 navigates distal end 40 into cavity 37 by manipulating catheter 22 with a manipulator 32 near the proximal end of the catheter as shown in an inset 23. The proximal end of catheter 22 is connected to interface circuitry in processor 39.

In some embodiments, the position of the distal end in cavity 37 is measured by a position sensor (not shown) of a magnetic position tracking system. The measured position serves as the coordinate of the respective map point.

For example, the anatomical measurements may be acquired using the fast anatomic mapping (FAM) functions of the CARTO® 3 System cooperatively with a mapping catheter such as the Navistar® Thermocool® catheter, both available from Biosense Webster, Inc., 3333 Diamond Canyon Road, Diamond Bar, Calif. 91765.

In this case, console 24 comprises a driver circuit 34, which drives magnetic field generators 36 placed at known positions external to patient 28 lying on table 29, e.g., below the patient's torso. The position sensor is fitted to the distal end, and configured to generate position signals in response to sensed external magnetic fields from field generators 36. The position signals are indicative of the position the distal end in the coordinate system of the position tracking system.

This method of position sensing is implemented in various medical applications, for example, in the CARTO™ system, produced by Biosense Webster Inc. (Diamond Bar, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

In some embodiments, physician 30 may use processor 39 for navigating distal end 40 to a target location and for activating the electrodes so as to sense and/or ablate the tissue at cavity 37. In alternative embodiments, processor 39 may be used only for assisting physician 30 in mapping unvisited regions and in estimating the quality of the anatomical mapping.

Processor 39, typically comprises a general-purpose computer, which is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

Interactive Anatomical Mapping by Indicating Unvisited Regions

FIG. 2 is a schematic, pictorial illustration of an anatomical map 41 of cavity 37 and a visualization scheme that directs physician 30 toward unmapped areas of cavity 37, in accordance with an embodiment of the present invention. In some embodiments, processor 39 receives anatomical data of heart 26 and uses the anatomical data to display an estimated volume 42 of cavity 37 in heart 26. In an embodiment, volume 42 may be displayed schematically as a cubical shape, or using any other suitable shape.

In some embodiments, processor 39 further receives from distal end 40 partial anatomical mapping, comprising multiple measurements, such as fast anatomical mapping (FAM), acquired at multiple respective locations within cavity 37. In an embodiment, based on these measurements, processor 39 is configured to compute an estimated partial surface 46 that was already mapped in cavity 37.

In an embodiment, using estimated volume 42 and the measurements already acquired, processor 39 is further configured to identify an unvisited region of cavity 37, such as an estimated surface 44, which was not yet mapped by the partial anatomical mapping. In the present context, the term "unvisited region" refers to regions of the surface of cavity 37 that are not yet represented by estimated partial surface 46.

In some embodiments, processor 39 displays on anatomical map 41 the position of distal end 40 as received from the position tracking system, and an arrow 48 that indicates the direction of the unvisited region, so as to assist physician 30 to complete the mapping of the tissue of cavity 37.

In other embodiments, processor 39 overlays a grid of three-dimensional (3D) pixels, also known as voxels (not shown), over volume 42. In this embodiment, processor 39 samples part of the voxels within volume 42 and identifies the voxels not yet visited by distal end 40. Then, processor 39 displays arrow 48 that indicates the direction of the unvisited voxels.

In some embodiments, processor 39 may display surface 44 of the unvisited region based on the measurements acquired at surface 46 and volume 42. In other embodiments, processor may display only surface 46, distal end 40, and arrow 48 so as to indicate the direction of the unvisited region to physician 30 without extrapolating the measurements acquired for estimating surface 46.

In an embodiment, processor 39 defines a given volume (not shown) that extends outward from distal end 40 and identifies locations within the given volume that were not yet visited by distal end 40. Then, processor 39 displays arrow 48 that indicates the direction of the unvisited locations within the given volume, so as to assist physician 30 to complete the mapping of the tissue of cavity 37.

Estimating the Quality of the Anatomical Mapping

FIG. 3 is a schematic, pictorial illustration of an estimated anatomical map 43, in accordance with an embodiment of the present invention. In some embodiments, for generating anatomical map 43, processor 39 receives multiple anatomical measurements, such as fast anatomical mapping (FAM), acquired at multiple respective locations within cavity 37.

Based on the measurements, processor 39 computes an estimated surface 45 and displays surface 45 in anatomical map 43 on display 35. Note that the computation of surface 45 is based on sampling measurements rather than continuous mapping of surface 45. In some embodiments, the computation of surface 45 may involve interpolation of the sampling measurements acquired therein, therefore, at least parts of surface 45 as displayed in map 43 may be inaccurate. For example, an interpolated region between multiple measurements may comprise an unvisited anatomical feature (e.g., bump or crater) that may deviate from the estimated topography made by processor 39.

In some embodiments, physician 30 may define a 3D shell 52 that extends inwards from estimated surface 45 into the internal volume of cavity 37. The shape of shell 52 may be defined by processor 39 using various methods. For example, processor 39 defines a virtual surface 50 parallel to surface 45 at a predefined distance (e.g., 7 mm) set by physician 30 or by processor 39. In this embodiment, the volume of shell 52 is confined between the boundaries of surfaces 45 and 50. In an embodiment, the volume of shell 52 is used for estimating the anatomical mapping quality of surface 45 as depicted in FIG. 4 below.

FIG. 4 is a schematic, pictorial illustration of a scheme for estimating the quality of anatomical map 43, in accordance with embodiments of the present invention. In some embodiments, processor 39 displays on anatomical map 43 surfaces 45 and 50, shell 52, and measurements 54 acquired by visiting selected locations at surface 45, using distal end 40 as described in FIGS. 1-3 above.

In some embodiments, processor 39 is configured to select within the volume of shell 52 one or more slices, such as slices 56 and 58. The slices may be selected randomly by processor 39, or according to a predefined parameter (e.g., specific locations within shell 52) set manually by physician 30 or automatically by processor 39.

In an embodiment, each slice represents a subsurface or a sub-volume within shell 52 comprising multiple pixels. In the example of FIG. 4, each slice comprises nine pixels depicted for the sake of clarity. In practice, each slice may comprise any suitable number of pixels.

In some embodiments, each slice may comprise pixels 55 representing measurements 54 falling within the respective slice. In an embodiment, processor 39 is configured to check the portion of pixels 55 falling within each slice so as to estimate the quality of the anatomical mapping represented by surface 45. In an embodiment, insets 66 and 68 represent the distribution of pixels 55 within slices 56 and 58, respectively. In general, a highly populated slice represents a high mapping quality and vice versa.

In inset 66, it appears that pixels 55 represent the majority of pixels (e.g., eight out of nine) of slice 56, therefore, slice 56 may get a high score (e.g., 89% (derived as 8/9=0.89) indicating high quality of the anatomical mapping on the left side of map 41. Using the same methodology, only two pixels 55 fall within slice 58, and the score of slice 58 is 22% (derived by counting 2 pixels out of 9), indicating low quality of the anatomical mapping in the upper central region of anatomical map 41.

In some embodiments, based on the scoring methodology described above, processor 39 is configured to display a quantitative map representing the quality of the anatomical mapping for each region of cavity 37. In an embodiment, physician 30 may set one or more quality thresholds so that processor 39 provides physician 30 with alerts in case of lower than desired quality of the anatomical mapping at specific locations of cavity 37. In other embodiments, slices 56 and 58 may represent volumetric elements rather than two-dimensional (2D) surfaces, so that pixels 55 may represent voxels (not shown), rather than 2D pixels.

Although the embodiments described herein mainly address cardiology applications, the methods and systems described herein can also be used in other applications, such as in ear-nose-throat (ENT), and bronchoscopy.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising:
receiving an anatomical mapping, comprising multiple measurements acquired at multiple respective locations within an organ of a patient, the multiple measurements including a physiological property of the organ acquired by an electrode at the multiple respective locations, and 3-D coordinates of the multiple respective locations;
computing an estimated surface of the organ based on the measurements;
defining a three-dimensional (3D) shell of the organ, which extends inwards from the estimated surface of the organ and has a predefined thickness; and
estimating a quality of the anatomical mapping, based on the measurements whose locations fall within the 3D shell.

2. The method according to claim 1, wherein defining the 3D shell comprises forming, at a predefined distance inwards from the estimated surface, a virtual surface confining the shell between the estimated surface and the virtual surface.

3. The method according to claim 1, wherein estimating the quality of the anatomical mapping comprises counting a number of the measurements whose locations fall within at least part of the shell.

4. The method according to claim 3, wherein the shell comprises multiple volume pixels (voxels), and wherein estimating the quality is based on a number of the voxels, within the at least part of the shell, in which the measurements fall.

5. The method according to claim 3, wherein the shell comprises a surface comprising multiple pixels, and wherein estimating the quality is based on a number of the pixels, within the at least part of the shell, in which the measurements fall.

6. The method according to claim 1, wherein the organ comprises a cavity of a heart.

7. Apparatus, comprising:
an interface; and
a processor, configured
to receive from the interface an anatomical mapping, comprising multiple measurements acquired at multiple respective locations within an organ of a patient, the multiple measurements including a physiological property of the organ acquired by an electrode at the multiple respective locations, and 3-D coordinates of the multiple respective locations,
to compute an estimated surface of the organ based on the measurements, to define a three-dimensional (3D) shell of the organ, which extends inwards from the estimated surface of the organ and has a predefined thickness, and
to estimate a quality of the anatomical mapping, based on the measurements whose locations fall within the 3D shell.

8. The apparatus according to claim 7, wherein the processor is configured to form, at a predefined distance inwards from the estimated surface, a virtual surface confining the shell between the estimated surface and the virtual surface.

9. The apparatus according to claim 7, wherein the processor is configured to estimate the quality based on a number of the measurements whose locations fall within at least part of the shell.

10. The apparatus according to claim 9, wherein the shell comprises multiple volume pixels (voxels), and wherein the processor is configured to estimate the quality based on a number of the voxels, within the at least part of the shell, in which the measurements fall.

11. The apparatus according to claim 9, wherein the shell comprises a surface comprising multiple pixels, and wherein the processor is configured to estimate the quality based on a number of the pixels, within the at least part of the shell, in which the measurements fall.

12. The apparatus according to claim 7, wherein the organ comprises a cavity of a heart.

* * * * *